US005830411A

United States Patent [19]

[11] Patent Number: 5,830,411
[45] Date of Patent: Nov. 3, 1998

Martinell Gisper-Sauch

[54] DEVICE FOR CARRYING OUT ERYTHROCYTIC REACTIONS

[75] Inventor: Enrique Martinell Gisper-Sauch, Barcelona, Spain

[73] Assignee: Grupo Grifols, S.A., Partes del Valles, Spain

[21] Appl. No.: 783,927

[22] Filed: Jan. 17, 1997

[30] Foreign Application Priority Data

Feb. 26, 1996 [ES] Spain .................................... 9600442

[51] Int. Cl.[6] .............................. G01N 33/00; B01L 3/00

[52] U.S. Cl. .............................. 422/73; 422/99; 422/102; 435/286.5; 435/288.3; 435/288.4; 435/288.5; 436/69

[58] Field of Search ................................. 422/72, 73, 99, 422/102; 435/286.4, 286.5, 288.3, 288.4, 288.5; 436/45, 69, 177

[56] References Cited

U.S. PATENT DOCUMENTS

| | | | |
|---|---|---|---|
| 4,671,939 | 6/1987 | Mintz | 422/58 |
| 5,244,635 | 9/1993 | Rabson et al. | 422/72 |
| 5,318,748 | 6/1994 | Babson et al. | 422/72 |
| 5,338,689 | 8/1994 | Yves et al. | 422/102 X |
| 5,472,671 | 12/1995 | Nilsson et al. | 422/102 |
| 5,491,067 | 2/1996 | Setcavage et al. | 422/73 X |
| 5,552,064 | 9/1996 | Chachowski et al. | 436/177 X |
| 5,650,068 | 7/1997 | Chachowski et al. | 436/177 X |
| 5,665,558 | 9/1997 | Frame et al. | 422/72 X |

FOREIGN PATENT DOCUMENTS 0 163 063 A2 12/1985 European Pat. Off. .

*Primary Examiner*—Maureen M. Wallenhorst
*Attorney, Agent, or Firm*—Darby & Darby

[57] ABSTRACT

The present invention provides a device for carrying out erythrocytic reactions, wherein the device includes a molded plate having multiple individual reaction compartments, each formed by an upper and lower chamber. The upper chamber is adapted to receive liquid for the first phase of the erythrocytic reaction which consists of dispensing reagents and samples, and the lower chamber contains a separating medium and reagents for the second phase of the reaction, wherein one or more products of the first phase are contacted with the contents of the lower chamber. The upper chamber communicates with the lower chamber through a narrow gap having a controlled width, such that the meniscus formed by surface tension prevents passage of the liquid in the upper chamber to the lower chamber, wherein centrifugation triggers the passage of liquid from one chamber to another.

7 Claims, 6 Drawing Sheets

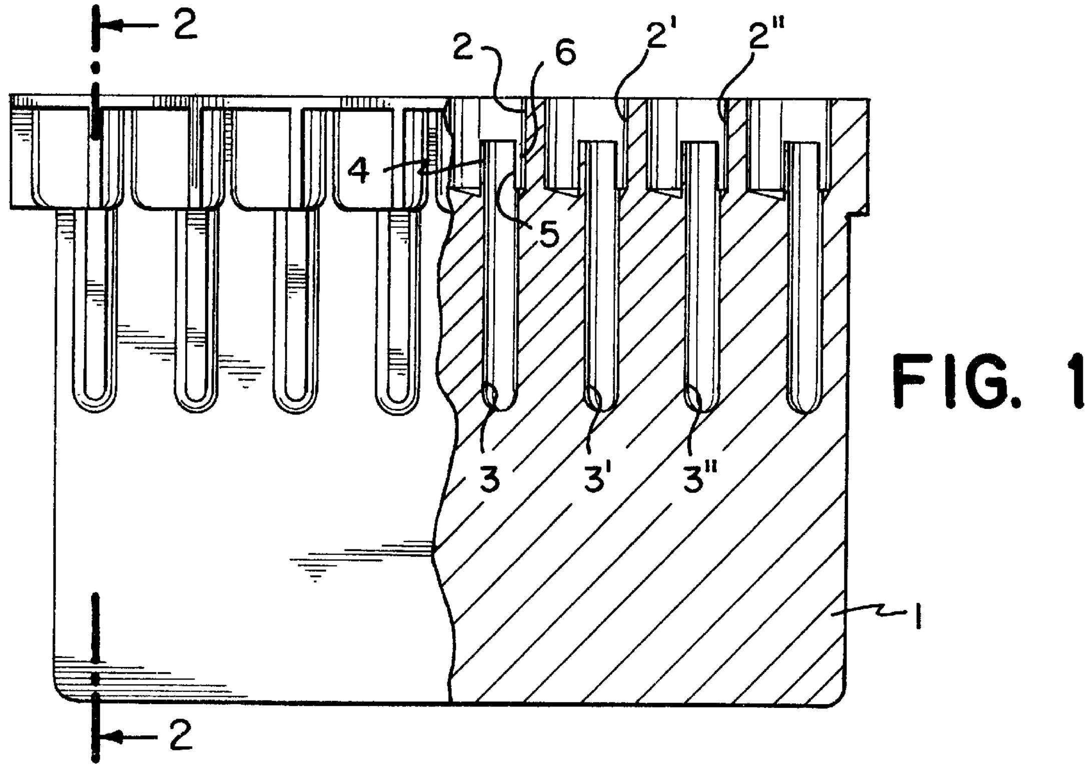
FIG. 1
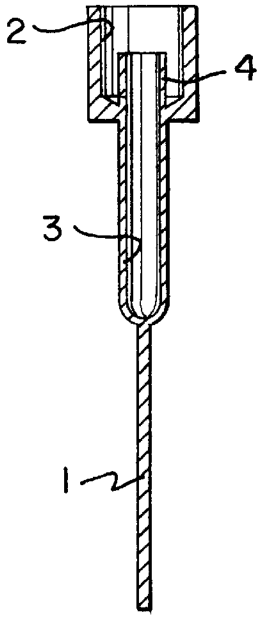
FIG. 2
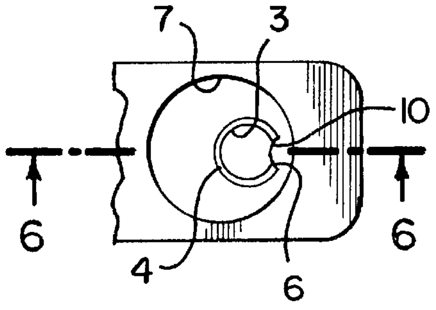
FIG. 7
FIG. 3
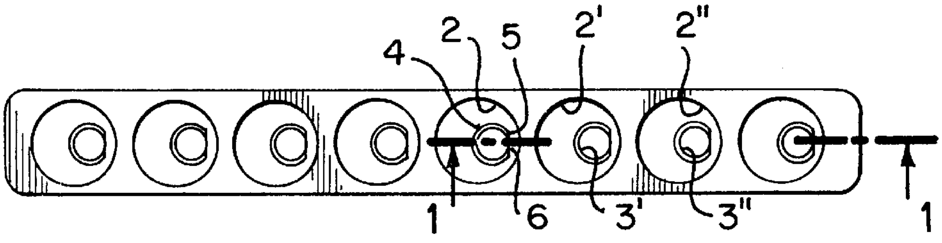

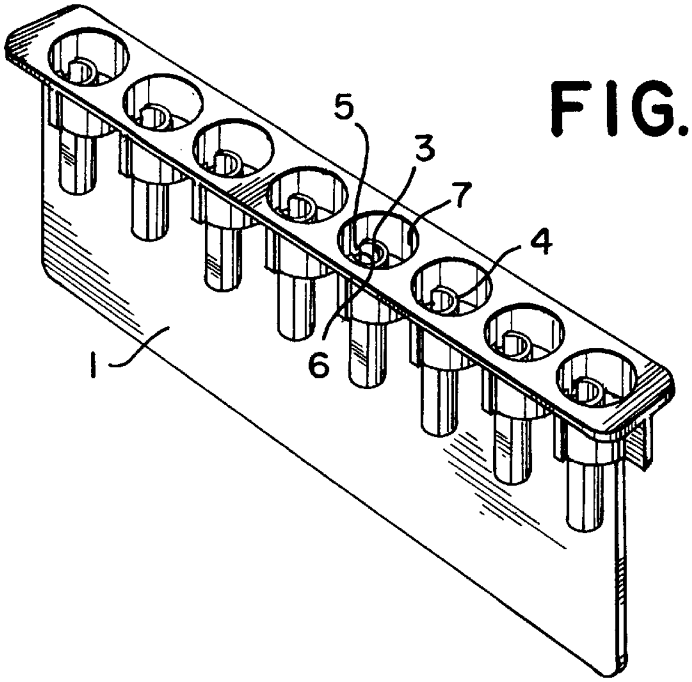
FIG. 4
FIG. 6
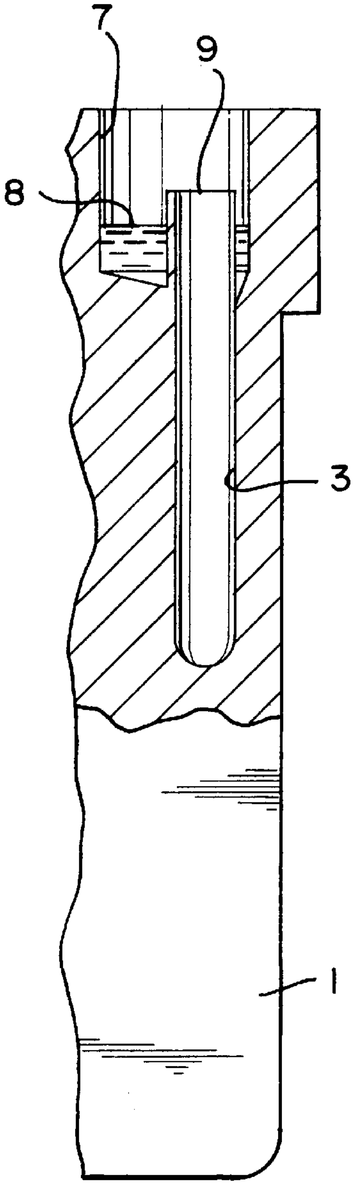
FIG. 5
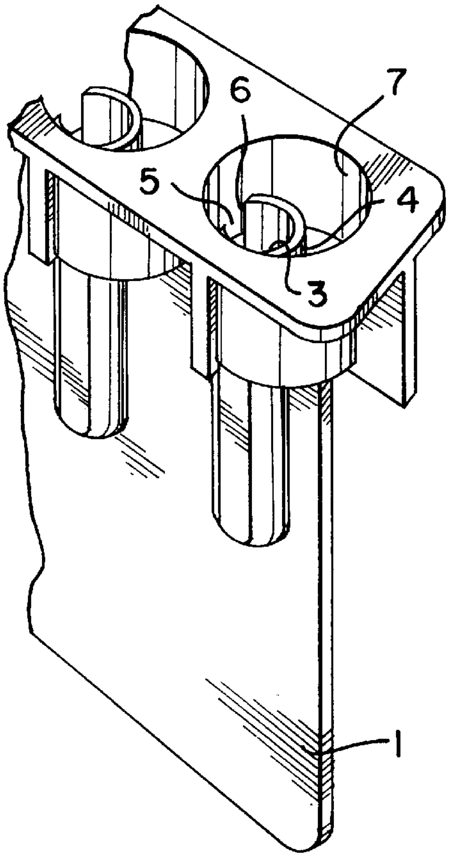

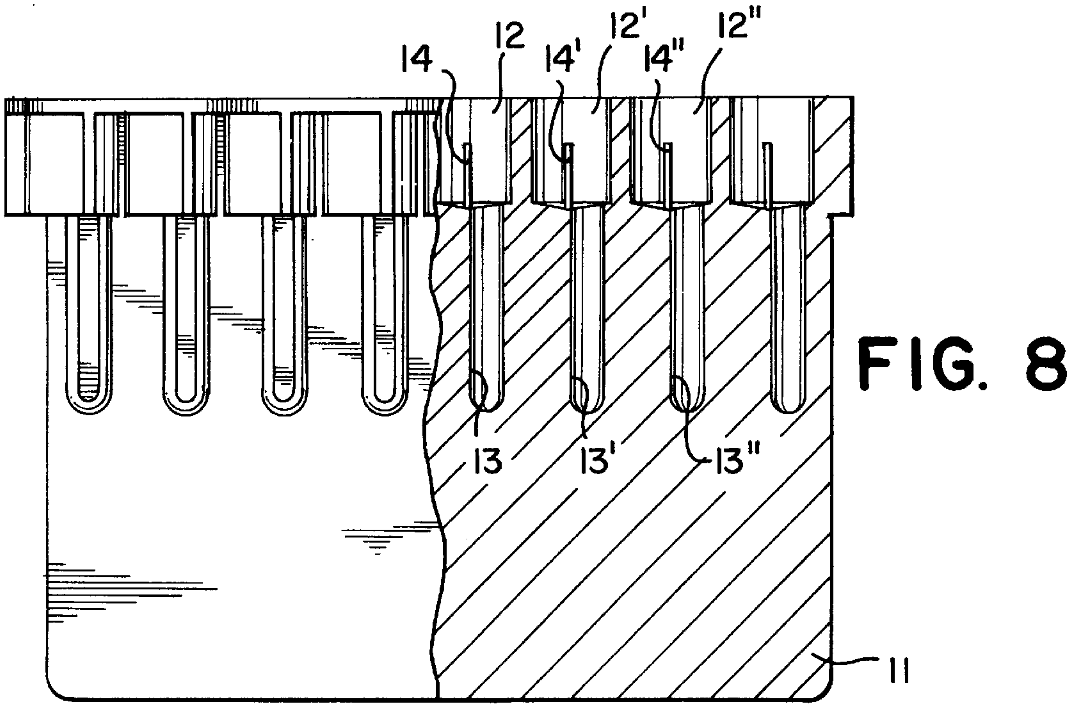
FIG. 8
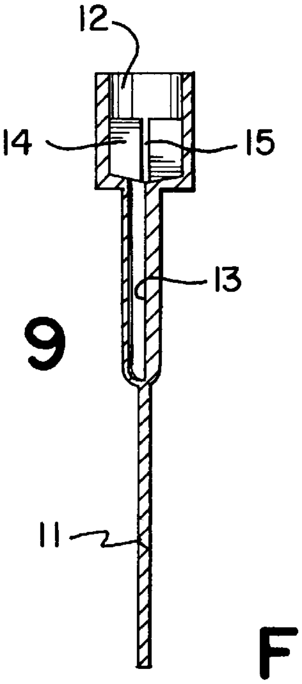
FIG. 9
FIG. 14
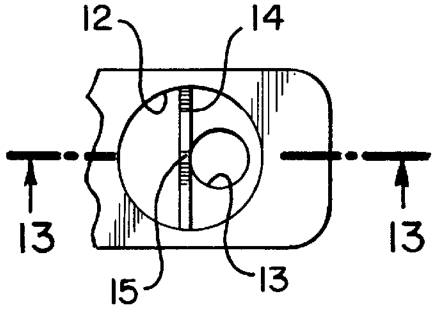
FIG. 10
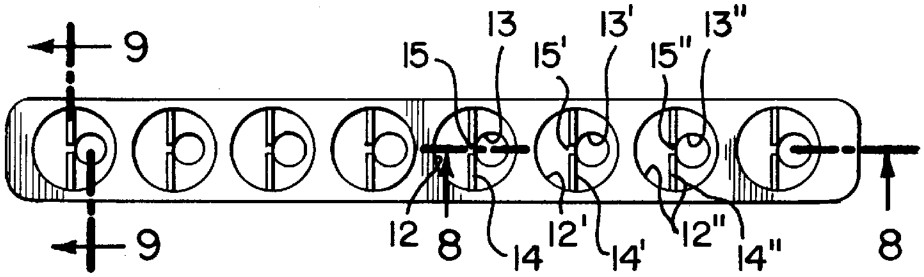

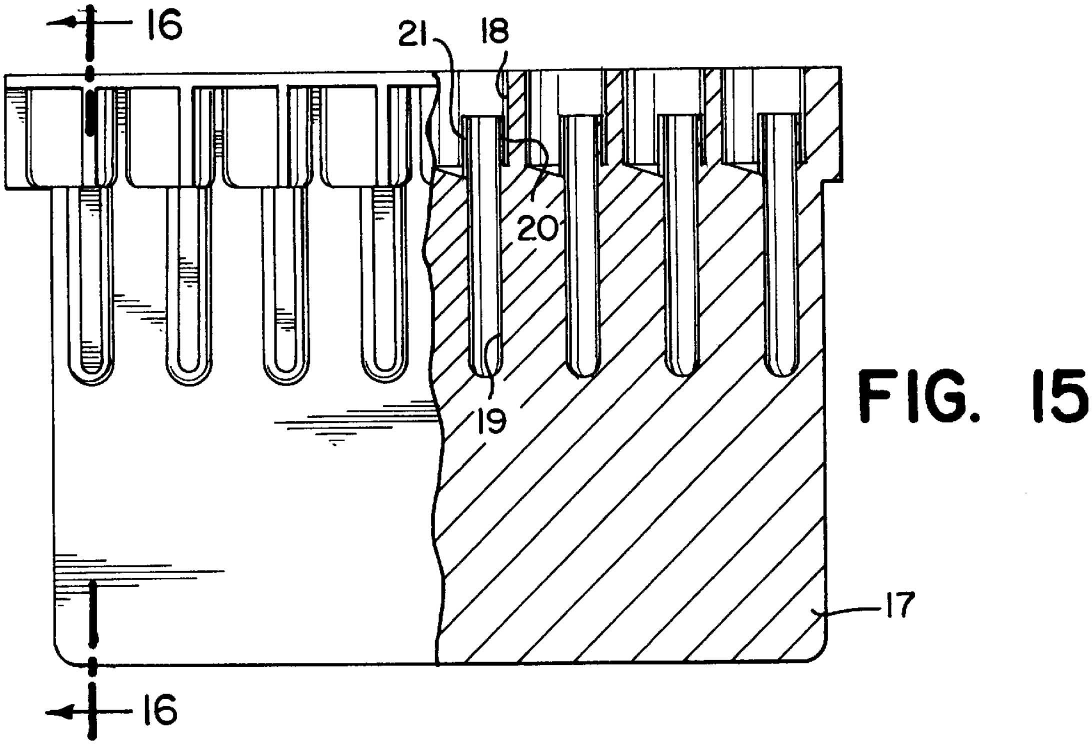
FIG. 15
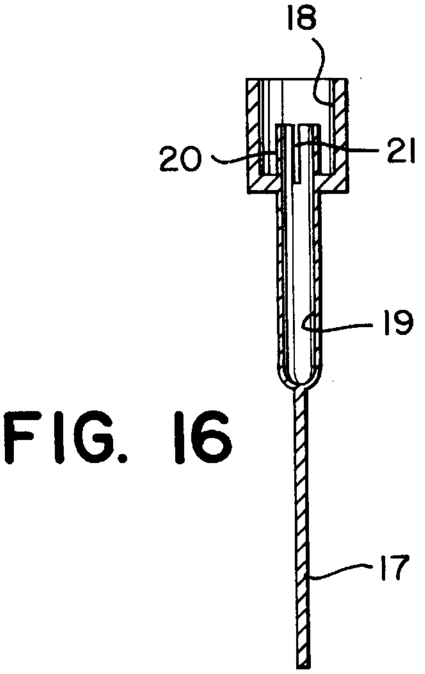
FIG. 16
FIG. 21
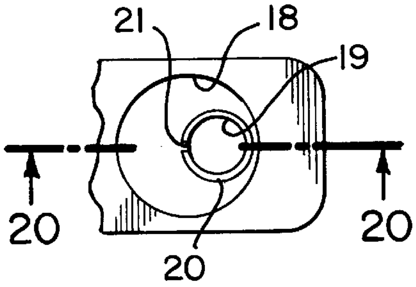
FIG. 17
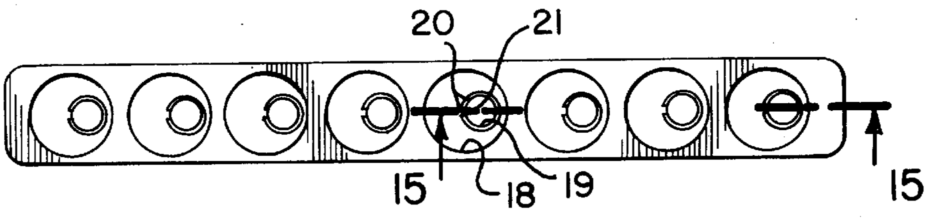

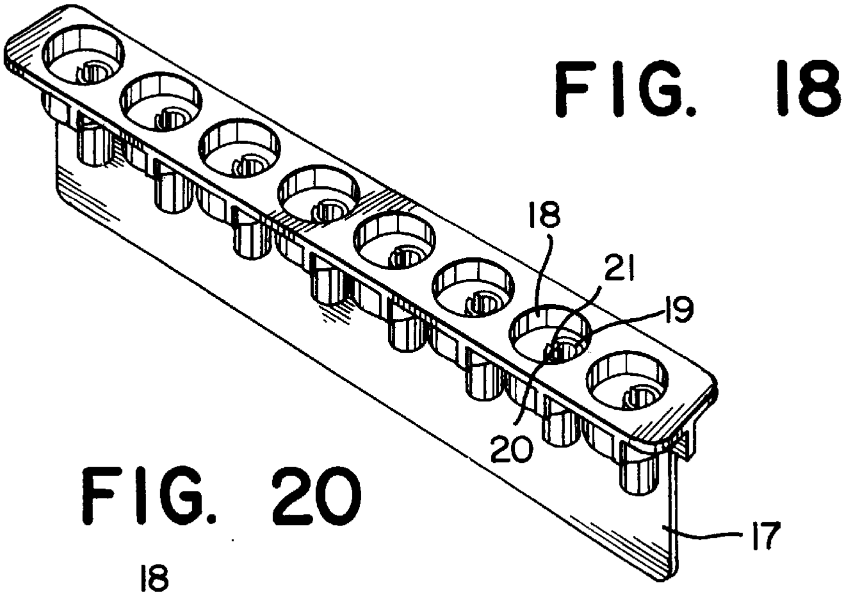
FIG. 18
FIG. 20
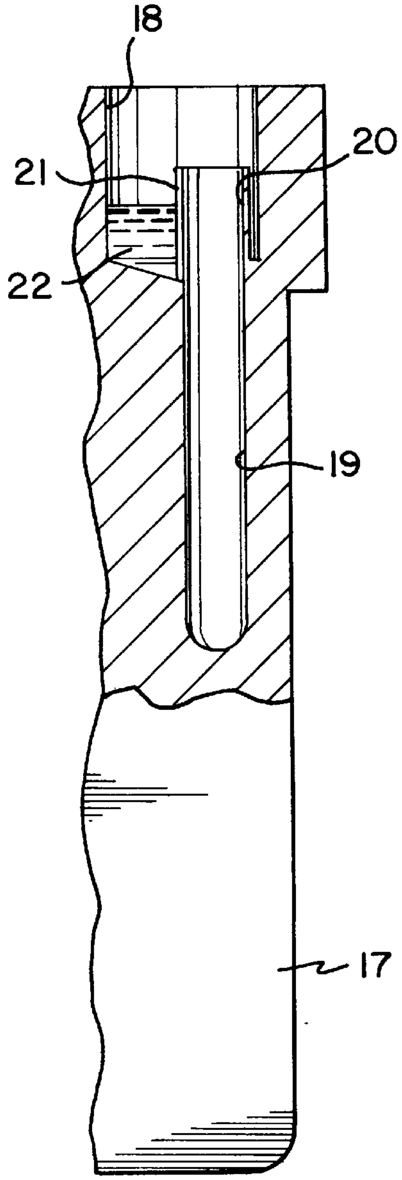
FIG. 19
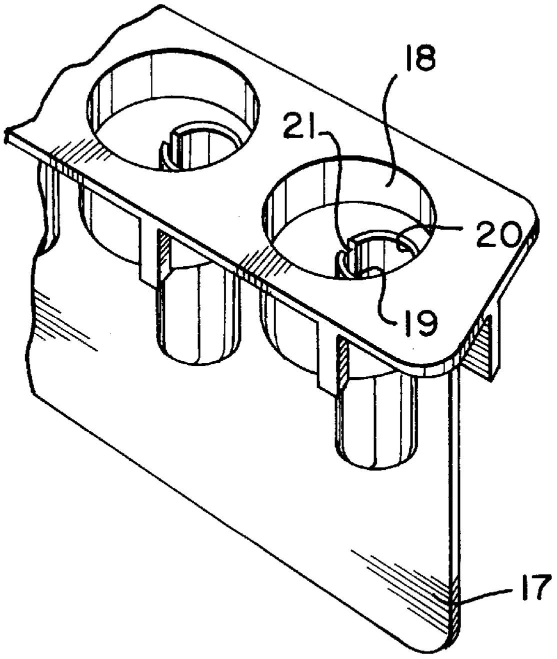

DEVICE FOR CARRYING OUT ERYTHROCYTIC REACTIONS

The present invention relates to a device for carrying out erythrocytic reactions which has substantial characteristics of novelty and inventive activity in comparison with that known at present.

BACKGROUND OF THE INVENTION

Immunohaematological tests are based on the detection of the possible agglutination of some haemocytes determined when they are in contact with a patient's serum or plasma or with a determined antiserum.

At present, the tests employed to classify blood and/or to determine its compatibility are:

Cross test: this is one of the most important techniques in blood transfusions. A cross test is carried out to determine the compatibility between haemocytes and serum of different persons facing a transfusion.

Investigation and identification of irregular antibodies: this is carried out with known reactive haemocytes and serum of a patient.

Direct group: this is carried out with a patient's haemocytes and a commercial reactive antiserum.

Reverse group: this is carried out with a patient's serum and commercial reactive haemocytes.

Self check: the haemocytes and serum are from the same patient.

Immunohaematological reactions of haemocyteserum agglutination normally occur in the presence of certain reagents such as enzymes and/or antiglobulins. Once the reaction has taken place, the agglutinated haemocytes can pass by centrifugation through a separating medium (for example gel) which allows the presence of agglutinated haemocytes to be detected.

Generally speaking, there are two distinct phases in the above-mentioned tests:

1st phase: When the reagents and samples are dispensed, producing the first part of the reaction.

2nd phase: When the product of the first phase comes into contact, due to centrifugation, with the separating medium which contains its own reagents, and the agglutinated substances are separated while other reactions can also take place at the same time.

During the investigation and identification of irregular antibodies, cross tests and self-checks, commercial haemocytes or haemocytes originating from the patient, patient's serum and, in some cases, other reagents are placed in the reaction chamber in the first phase. There is an incubation period when there must be no contact with the separating medium and its reagents (for example antiglobulin) to prevent the inactivation thereof.

In the second phase of the reaction, triggered by centrifugation, the agglutinated haemocytes are separated from those which are not agglutinated, while other reactions are taking place in the interior of the separating medium.

During tests on direct groups in the reaction chamber, the patient's haemocytes and other reagents or diluents are dispensed, an incubation period being necessary during which the haemocytes must not come into contact with the antiserum contained in the separating medium before the second phase of the reaction is carried out.

However, it is important to prevent the reagents and samples from the first phase from coming into contact with the separating medium and its reagents until said first phase has ended.

Up until now, the techniques employed for immuno-haematological reactions by this method utilize a container formed by a plurality of cups, each of which consists of a column or microtube filled with the separating medium, closed at the bottom and connected by the top to a cavity of greater diameter by means of a conical connection.

The reagents and/or samples are supplied or dispensed in the upper cavity, a first stage of the immuno-haematological reaction taking place in this cavity during a so-called incubation period.

Centrifugation is then carried out to enable the haemocytes to pass to the lower microtube and a second reaction takes place with the reagents contained in the separating medium which may or may not be retained in the separating medium, giving the result of the test.

The problem with these containers (Diamed, Diagast, Ortho, Gamma, Sanofi Pasteur . . . ) is that some of the components which are dispensed into the cup come into contact with the separating medium and its reagents before completing the first part of the reactions, for example if haemocytes and then antiserum are dispensed, the haemocytes can come into contact with the separating medium before the antiserum has been dispensed, so the test results may be inaccurate.

At present, this problem is avoided by means of various systems, including:

1. Allowing little time to elapse between the dispensing of the various reagents or samples, avoiding time for an undesirable reaction to take place.
2. Dispensing the reagents and/or sample so as to avoid the above-mentioned contact, for example dispensing them so as to form a bubble in the upper part of the separating medium which prevents contact between the two phases. This can be achieved by carefully dispensing obliquely against the wall of the upper cavity or another system depending on the geometry of the container.

These systems limit the safety of the device and complicate manual use of the techniques and the automation thereof.

To overcome the above-mentioned drawbacks, the inventor of the present patent application has carried out investigations and laboratory tests to obtain a device for carrying out erythrocytic reactions which prevents the reagents and samples from the first phase from coming into contact with the separating medium and its reagents before said phase has ended.

SUMMARY OF THE INVENTION

To achieve its object, the present invention proposes the design of the cups of the container, whatever it may be, wherein the upper cavity is separated from the upper orifice of the microtube by one or more apertures which are sufficiently narrow to guarantee that the reagents and/or haemocytes which are dispensed are retained in the upper cavity during the first part of the reaction and will only overcome this barrier or limitation by means of the subsequent centrifugation and will be introduced into the microtube in order to come into contact with the separating medium. In this way, the duration of the first phase can be controlled as desired, preventing the reagents and samples from coming into contact improperly with the separating medium. The orifices or apertures in the upper cavity of the cup of the container will be sufficiently small to guarantee that, owing to the surface tension generated, the dispensed reagents and/or haemocytes are retained in the upper cavity for the first part of the reaction and will only overcome this barrier by means of centrifugation and will be introduced into the microtube, coming into contact with the separating medium in a totally controlled manner.

The variations proposed by the invention include, in particular, a variation in which the lower cup of the element is extended in a tubular manner eccentrically into the upper chamber for receiving the reagents, said extension having a groove, openings or general communication between the above-mentioned characteristics which prevents the escape of the reagents from the upper chamber toward said cup due to the action of the surface tension created by the liquids deposited in said upper chamber.

The eccentricity of the extension of the cup with respect to the upper chamber determines dimensions which are greater for the optionally automated pouring of the liquids for the first phase of the reaction.

In a further variation of the present invention, the chamber in which the liquids are deposited for the first reaction will have a transverse baffle of variable shape which will carry the gaps or grooves of variable shape with suitable dimensions for avoiding natural passage, this being prevented by the action of the surface tension.

Many other variations can be produced within the scope of the present invention invariably with the essential characteristic that the upper chamber for the first phase of the reaction is separated from the lower cup carrying the separating medium in which the second phase of the reaction is carried out by means of narrow gaps or grooves in which the film or meniscus formed by surface tension of liquid prevents the free passage thereof toward the cup, allowing the passage of liquid to the second phase of the reaction to be suitably controlled at the desired moment, passage being permitted by the action of centrifugation.

To sum up, therefore, the present invention comprises a molded plate with a plurality of individual reaction compartments formed by an upper chamber and a lower cup intended to contain the separating medium and reagents, characterized in that the upper reaction chamber receiving the liquids for the first phase of the reaction communicates with the lower cup carrying the separating medium by means of a narrow gap of which the width is controlled so that the meniscus formed by surface tension prevents the passage of the liquid contained freely to the cup, the liquid being able to pass to the cup merely by the action of centrifugation.

The gap for communication between the upper reagent chamber and the corresponding cup preferably adopts the form of a straight groove.

The drawings of explanatory, non-limiting embodiments of the present invention are attached by way of example to assist understanding thereof.

BRIEF DESCRIPTION OF THE FIGURES

FIGS. 1 and 2 are front elevations with a partial section and cross section of a plate for carrying out erythrocytic reactions in accordance with the present invention.

FIG. 3 is a plan view of the embodiment in FIGS. 1 and 2.

FIG. 4 is a perspective view of the plate shown in FIGS. 1 to 3 rotated 180° for purposes of clarity.

FIG. 5 shows a detail of the plate in FIGS. 1 to 4 in perspective rotated 180° with respect to FIGS. 1 to 3 for purposes of clarity.

FIGS. 6 and 7 show details in a longitudinal section and in a plan view of the variation of FIGS. 1 to 5 with the liquid poured into the main cavity.

FIGS. 8, 9 and 10 are elevations with section, cross section and plan view of a second embodiment of the present invention.

FIGS. 13 and 14 show details in a longitudinal section and plan view of the embodiment in FIGS. 8 to 10 showing the liquid situated in the main chamber.

FIGS. 15 to 17 are elevations with section, cross section and plan view of a third embodiment as an example of the present invention.

FIGS. 18 and 19 are perspective views illustrating design details of the plate according to the present invention corresponding to FIGS. 15, 16 and 17.

FIGS. 20 and 21 are a longitudinal section and plan view of the embodiment corresponding to FIGS. 16 to

DETAILED DESCRIPTION OF THE PREFERRED EMBODIMENTS

Figure 11:
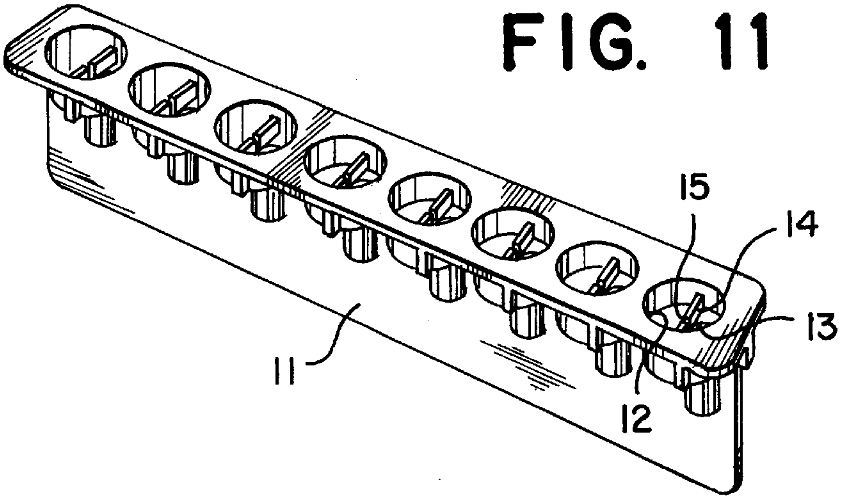
FIGS. 11 and 12 are perspective views of the embodiment shown in FIGS. 8 to 10.

As shown in the drawings, the device forming the subject of the present application comprises, as shown in the drawings, a plate 1 carrying a plurality of main cavities such as 2, 2', 2". . . , each of which has a lower eccentric reaction cup indicated by the numerals 3, 3', 3". . . . A characteristic of the present invention is that each upper chamber 2 and its corresponding cup 3 is connected by means of a gap or groove with controlled dimensions of a linear, rectilinear or other type, so that the upper layer or meniscus formed by surface tension of the liquid contained in the main reaction chamber prevents the passage of said liquid toward the cup in an uncontrolled manner, this passage merely taking place in the phase of controlled centrifugation. In the embodiment shown in FIG. 1, each of the tubular cups 3, 3', 3" is extended at the top by a tubular portion of small length 4 which is arranged eccentrically with respect to the upper reaction chamber 2 and has a longitudinal orifice 5 producing the above-mentioned gap effect.

At the moment when the reaction liquid is deposited in said chamber 2, FIG. 1, the liquid will accumulate at a variable level 8, FIGS. 6 and 7, below the upper level 9 of the upper cylindrical extension 4 not passing through the aperture 10 owing to the action of the surface tension of the liquid.

In a further variation shown in FIGS. 8 to 12, the plate 11 has a plurality of upper reaction chambers such as 12, 12', 12". . . , each of which is connected to a lower cup 13, 13', 13". . . preferably arranged eccentrically and having a transverse baffle like those indicated in FIG. 10 by numerals 14, 14', 14". . . having fine grooves such as 15, 15', 15". . . which form the same above-mentioned function of preventing the free passage of the liquid due to the action of surface tension, said resistance being overcome by the action of centrifugation.

Figure 13:
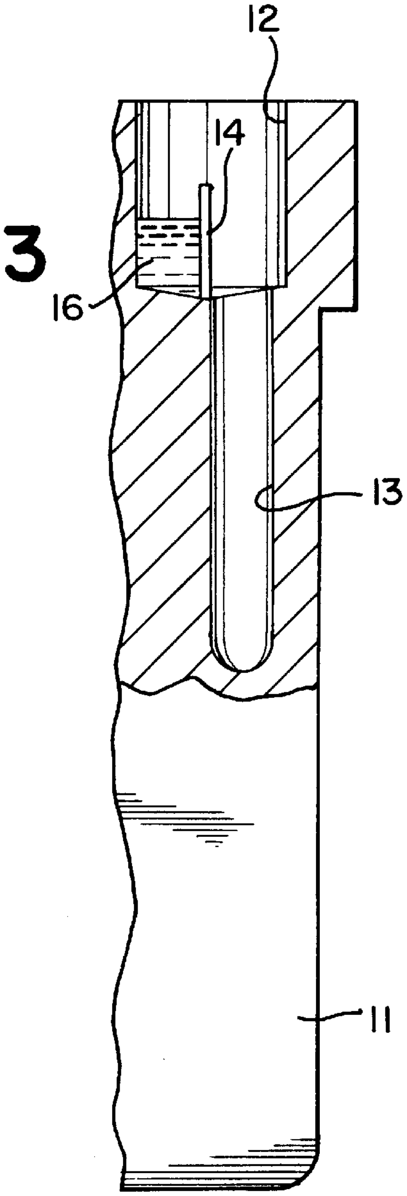
Figure 12:
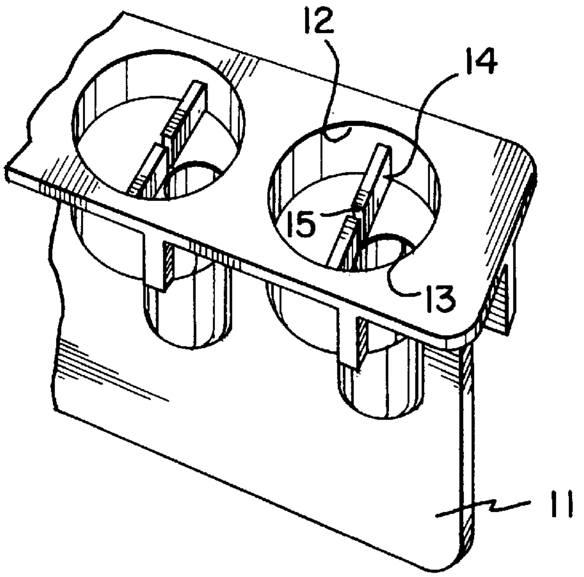

The arrangement of the mass of reaction liquid 16, FIGS. 13 and 14, allows the time required for the first phase of the reaction which subsequently passes through the groove 15 at the moment of centrifugation.

In a further embodiment shown in FIGS. 15 to 21, the plate 17 has a plurality of upper reaction chambers of which one is indicated by the numeral 18 which are connected to the cups such as 19, the cup being extended at the top by a cylindrical portion 20 having a groove 21 to allow the above-mentioned capillary action.

The mass of liquid 22 arranged in the reaction chamber will also be retained by the action of surface tension of the liquid in this case.

In all the aforementioned cases, the eccentric arrangement of the cup with respect to the upper chamber will be an arrangement which is particularly favorable for greater dimensions of said upper chamber to facilitate the automatic pouring of the reagents.

I claim:

1. A device for carrying out an erythrocytic reaction comprising a molded plate having a plurality of individual reaction compartments each formed by an upper chamber and a lower chamber;

wherein said upper chamber is adapted to receive liquid for a first phase of the erythrocytic reaction which comprises the dispensing of reagents and samples into the upper chamber; and said lower chamber contains a separating medium and reagents for a second phase of said erythrocytic reaction;

wherein said upper chamber communicates with said lower chamber by means of a narrow gap in the form of a rectilinear groove having a controlled width, such that a meniscus formed by surface tension prevents passage of the liquid in said upper chamber to said lower chamber, said passage being triggered by centrifugation, whereby one or more products of the first phase of the erythrocytic reaction in the upper chamber are contacted with the separating medium and reagents in the lower chamber rotated 180° for purposes of clarity.

2. A device according to claim 1 wherein the upper chamber and the lower chamber are offset from one another to facilitate passage of the products of the first phase of the erythrocytic reaction into the lower chamber.

3. A device according to claim 2, wherein the rectilinear groove for communication between the upper chamber and the lower chamber is produced in an upper extension of the lower chamber which projects into an interior of the upper chamber.

4. A device according to claim 2, wherein the rectilinear groove for communication between the upper chamber and the lower chamber is produced by a transverse baffle contained in the upper chamber which separates the upper chamber from an upper mouth of the lower chamber.

5. A device according to claims 1, wherein the rectilinear groove for communication between the upper chamber and the lower chamber is produced in an upper extension of the lower chamber which projects into an interior of the upper chamber.

6. A device according to claim 1 wherein the rectilinear groove for communication between the upper chamber and the lower chamber is produced by a transverse baffle contained in the upper chamber which separates the upper chamber from an upper mouth of the lower chamber.

7.A device according to claim 1 wherein the upper chamber and the lower chamber are offset from one another to facilitate pouring of reagents into the upper chamber.

* * * * *